United States Patent [19]

Müller et al.

[11] Patent Number: 5,420,149

[45] Date of Patent: * May 30, 1995

[54] IMIDAZOLYL-SUBSTITUTED PHENYLACETAMIDES

[75] Inventors: Ulrich E. Müller, Wuppertal; Matthias Müller-Gliemann, Solingen Ohligs; Jürgen Dressel; Peter Fey, both of Wuppertal; Rudolf Hanko, Duesseldorf; Walter Hüsch; Thomas Krämer, both of Wuppertal; Martin Beuck, Erkrath; Stanislav Kazda, Wuppertal; Stefan Wohlfeil, Hilden; Özkan Yalkinoglu, Wuppertal; Andreas Knorr, Erkrath; Johannes-Peter Stasch, Wuppertal; Ulrich Niewöhner, Wermelskirchen, all of Germany

[73] Assignee: Bayer Aktiengesellschaft, Leverkusen, Germany

[*] Notice: The portion of the term of this patent subsequent to Apr. 15, 2011 has been disclaimed.

[21] Appl. No.: 25,493

[22] Filed: Mar. 3, 1993

[30] Foreign Application Priority Data

Mar. 13, 1992 [DE] Germany .................. 42 08 052.5

[51] Int. Cl.⁶ ............ A61K 31/415; C07D 233/68; C07D 233/60
[52] U.S. Cl. ............................. 514/399; 514/63; 548/110; 548/338.1; 548/340.1; 548/341.5
[58] Field of Search .......... 548/338.1, 340.1, 341.5, 548/110; 514/399, 63

[56] References Cited

U.S. PATENT DOCUMENTS

4,355,040 10/1982 Furukawa et al. ............ 424/273 R
4,946,841 8/1990 Baader et al. ............... 514/247

FOREIGN PATENT DOCUMENTS

0324377 7/1989 European Pat. Off. .
0399731 11/1990 European Pat. Off. .
0399732 11/1990 European Pat. Off. .
0407102 1/1991 European Pat. Off. .
9112002 8/1991 WIPO .

OTHER PUBLICATIONS

Hollenberg, Journal of Medicinal Chemistry, vol. 33, No. 5, 1312–1329 (1990).
R. V. Vitzgert, Uspekhi, Khimii 32, 1–20 (1963).
R. Ross, J. Cell, Biol. 50, 172–186 (1971).
J. C. Sheehan, et al., J. Am. Chem. Soc. 95, 875–879 (1973).
N. L. Benoiton, et al., Int. Pept. Prot. Res. 17, 197–204 (1981).
N. Bartlett et al., J. Chem. Soc., Chem. Commun., (2), 167–168 (1966).
Frerman et al, J. Biol. Chem. 258, 7087–7093 (1983).

*Primary Examiner*—Patricia L. Morris
*Attorney, Agent, or Firm*—Sprung Horn Kramer & Woods

[57] ABSTRACT

Imidazolyl-substituted phenylacetic acid derivatives are prepared by first reacting suitably substituted phenylacetic acid with imidazoles and subsequently converting the product into an amide. The compounds can be employed as active compounds in medicaments, in particular for treating hypertension and atherosclerosis.

8 Claims, No Drawings

IMIDAZOLYL-SUBSTITUTED PHENYLACETAMIDES

The invention relates to imidazolyl-substituted phenylacetamides, to processes for their preparation, and to their use in medicaments, in particular as antihypertensives and as antiatherosclerotic agents.

It is known that renin, a proteolytic enzyme, splits off in vivo the decapeptide angiotensin I from angiotensinogen, and angiotensin I, in turn, is broken down in the lungs, in the kidneys or in other tissues into the hypertensive octapeptide angiotensin II. The various effects of angiotensin II, such as, for example, vasoconstriction, $Na^+$ retention in the kidneys, secretion of aldosteron in the adrenal gland, and hypertonia of the sympathetic nervous system act synergistically in the sense of a rise in blood pressure.

Moreover, angiotensin II has the property of enhancing the growth and the multiplication of cells such as, for example, myocardial cells and smooth muscle cells, these cells undergoing increased growth and proliferation in a series of pathemata (e.g. hypertension, atherosclerosis and cardiac insufficiency.)

A possible way of engaging in the renin/angiotensin system (RAS) is, besides inhibiting the renin activity, the inhibition of the angiotensin conversion enzyme (ACE) activity as well as the blockade of angiotensin II receptors.

Moreover, heterocyclic compounds which act as A II antagonists are disclosed in the publications EP 407,102, EP 399,731; EP 399,732 and EP 324,347.

The invention relates to imidazolyl-substituted phenylacetamides of the general formula (I)

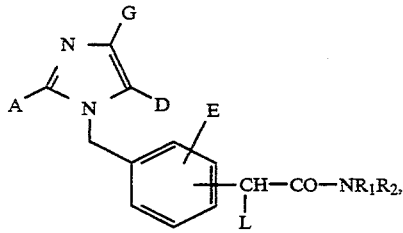

in which

A represents straight-chain or branched alkyl or alkenyl, each of which has up to 8 carbon atoms, or represents cycloalkyl having 3 to 8 carbon atoms, G represents hydrogen, halogen or perfluoroalkyl having up to 5 carbon atoms, D represents a group of the formula $-CH_2OR^3$, $-CO-R^4$, $-CO-NR^5R^6$,

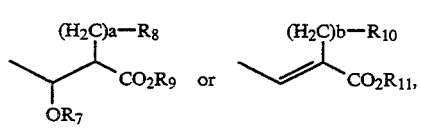

in which $R^3$ represents hydrogen or straight-chain or branched alkyl having up to 8 carbon atoms, $R^4$ represents hydrogen, hydroxyl or straight-chain or branched alkoxy having up to 8 carbon atoms, $R^5$ and $R^6$ are identical or different and represent hydrogen, straight-chain or branched alkyl having up to 8 carbon atoms, or $R^5$ has the abovementioned meaning and $R^6$ represents a group of the formula $-SO_2R^{12}$ in which $R^{12}$ represents straight-chain or branched alkyl having up to 6 carbon atoms, benzyl or phenyl, each of which is optionally substituted by straight-chain or branched alkyl having up to 6 carbon atoms, a and b are identical or different and represent a number 0, 1 or 2, $R^7$ represents hydrogen or straight-chain or branched alkyl having up to 8 carbon atoms, or a hydroxyl protective group, $R^8$ and $R^{10}$ are identical or different and represent hydrogen, straight-chain or branched alkyl having up to 6 carbon atoms, cycloalkyl having 3 to 8 carbon atoms, phenyl or thienyl, $R^9$ and $R^{11}$ are identical or different and represent hydrogen or straight-chain or branched alkyl having up to 8 carbon atoms, E represents hydrogen, halogen, nitro, hydroxyl, trifluoromethyl, trifluoromethoxy, straight-chain or branched alkyl, alkoxy or alkylcarbonyl, each of which has up to 6 carbon atoms, cyano or carboxyl, L represents straight-chain or branched alkyl which has up to 8 carbon atoms and which is optionally substituted by cycloalkyl having 3 to 8 carbon atoms or phenyl, or represents cycloalkyl which has 3 to 12 carbon atoms and which is optionally substituted by straight-chain or branched alkyl having up to 6 carbon atoms, $R^1$ represents hydrogen or straight-chain or branched alkyl having up to 8 carbon atoms, $R^2$ represents a radical of the formula $-C(CH_3)_2-CH_2OH$,

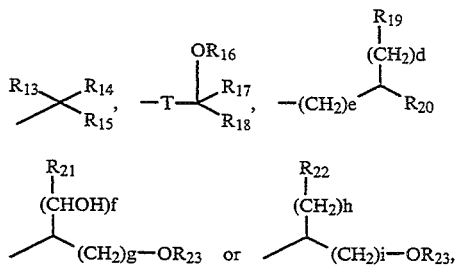

in which $R^{13}$ and $R^{14}$ are identical or different and represent hydrogen or straight-chain or branched alkyl having up to 8 carbon atoms, $R^{15}$ represents straight-chain or branched alkyl which has 2 to 8 carbon atoms and which may also optionally have to be up to trisubstituted by identical or different substituents from the series comprising hydroxyl, carboxyl, trifluoromethyl, halogen, nitro, cyano, by straight-chain or branched alkoxy, acyl or alkoxycarbonyl, each of which has up to 8 carbon atoms, or by aryl having 6 to 10 carbon atoms or by a 5- to 7-membered, saturated or unsaturated heterocycle or benzo-fused heterocycle having up to 3 hetero atoms from the series comprising S, N or O, it being possible for these substituents, in turn, to be up to disubstituted by identical or different substituents from the series comprising halogen, nitro, cyano, hydroxyl or by straight-chain or branched alkyl or alkoxy, each of which has up to 6 carbon atoms, or alkyl is optionally substituted by a group of the formula —CO—NR$^{24}$R$^{25}$ in which R$^{24}$ and R$^{25}$ have the abovementioned meaning of R$^5$ and R$^6$ and are identical therewith or different therefrom, or R$^{24}$ and R$^{25}$ together with the nitrogen atom form a 5- to 7-membered saturated or unsaturated heterocycle having up to 2 further hetero atoms from the series comprising S, N or O, or R$^{15}$ represents a straight-chain or branched alkoxy or alkoxycarbonyl having in each case up to 8 carbon atoms, hydroxyl, carboxyl, trifluoromethyl or the group of the formula —CO—NR$^{24}$R$^{25}$ in which R$^{24}$ and R$^{25}$ have the abovementioned meaning, T represents straight-chain or branched alkyl having from 2 up to 8 carbon atoms, is hydrogen or straight-chain or branched alkyl having up to 8 carbon atoms, R$^{17}$ and R$^{18}$ are identical or different and represent hydrogen, straight-chain or branched alkyl having up to 6 carbon atoms or phenyl, or R$^{17}$ and R$^{18}$ together form a saturated and/or unsaturated carbocyclic 2- or 3-membered ring, d represents a number 0, 1, 2, 3 or 4, e represents a number 1, 2, 3 or 4, f represents a number 1, 2, 3 or 4, g represents a number 1, 2, 3, 4, 5 or 6, h represents a number 0, 1, 2, 3, or 4, i represents a number 2, 3, 4 or 5, R$^{20}$ has the abovementioned meaning of R$^{15}$ and is identical therewith or different therefrom, or denotes the —CH$^2$OH group, R$^{19}$ R$^{21}$ and R$^{22}$ are identical or different and represent phenyl which is optionally up to trisubstituted by identical or different substituents from the series comprising halogen, hydroxyl, trifluoromethyl, or by straight-chain or branched alkyl or alkoxy, each of which has up to 8 carbon atoms, or by phenoxy or benzyloxy, R$^{23}$ and R$^{23'}$ are identical or different and represent hydrogen, straight-chain or branched alkyl or alkoxycarbonyl, each of which has up to 8 carbon atoms, and their salts.

The compounds of the general formula (I) according to the invention can also exist in the form of their salts. Salts which are mentioned here in general are those with organic or inorganic bases or acids.

Physiologically acceptable salts are preferred within the scope of the present invention. Physiologically acceptable salts of the heterocycle-substituted phenyl acetic acid derivatives can be salts of the substances according to the invention with mineral acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal salts or ammonium salts of those compounds according to the invention which have a free carboxylic group. Examples which are particularly preferred are sodium salts, potassium salts, magnesium salts or calcium salts as well as ammonium salts which are derived from ammonia or organic amines such as, for example, ethylamine, di- or triethylamine, di- or triethanolamine, dicyclohexylamine, dimethylaminoethanol, arginine, lysine or ethylenediamine. The compounds according to the invention can exist in stereoisomeric forms which are either as image and mirror-image (enantiomers) or not as image and mirror-image (diastereomers). The invention relates to the enantiomers or diastereomers as well as to their respective mixtures. The racemic forms, as well as the diastereomers, can be resolved in a known manner to give the stereoisomerically uniform components [cf. E. L. Eliel, Stereochemistry of Carbon Compounds, McGraw Hill, 1962].

Heterocycle or benzo-fused heterocycle generally represents a 5- to 7-membered, preferably 5- to 6-membered, saturated or unsaturated ring which can contain up to 2 oxygen, sulphur and/or nitrogen atoms as hetero atoms. 5- and 6-membered rings having one oxygen, sulphur and/or up to 2 nitrogen atoms are preferred. The following are mentioned as being preferred: thienyl, furyl, pyrrolyl, pyrazolyl, pyridyl, quinolinyl, tetrahydrofuranyl, tetrahydropyranyl, dihydrobenzopyranyl or dihydrobenzylfuranyl. Pyridyl, furanyl, thienyl, tetrahydrofuranyl or pyrrolidinyl are preferred. Carbocyclic two- and three-membered ring generally represents fluorenyl, naphthyl, indenyl, anthranyl or phenanthryl. Indenyl and fluorenyl are preferred. Hydroxyl protective group within the scope of the abovementioned definition generally represents a protective group from the series comprising: trimethylsilyl, triethylsilyl, triisopropylsilyl, tert-butyldimethylsilyl, tert-butyldiphenylsilyl, trimethylsilylethoxycarbonyl, benzyl, triphenylmethyl(trityl), monomethoxytrityl (MMTr), dimethoxytrityl, (DMTr),benzyloxycarbonyl, 2-nitrobenzyl, 4-nitrobenzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl or 4-methoxybenzoyl. Acetyl is preferred.

Preferred compounds of the general formula (I) are those in which

A represents straight-chain or branched alkyl or alkenyl, each of which has up to 6 carbon atoms, or represents cyclopropyl, cyclobutyl, cyclopentyl, cyclohexyl or cycloheptyl, B represents hydrogen, fluorine, chlorine, bromine or perfluoroalkyl having up to 4 carbon atoms, D represents a group of the formula —CH$_2$OR$^3$, —CO—R$^4$, —CO—NR$^5$R$^6$,

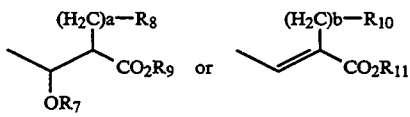

in which

R$^3$ represents hydrogen or straight-chain or branched alkyl having up to 6 carbon atoms, R$^4$ represents hydrogen, hydroxyl or straight-chain or branched alkoxy having up to 6 carbon atoms, $R^5$ and $R^6$ are identical or different and represent hydrogen, straight-chain or branched alkyl having up to 6 carbon atoms, or $R^5$ has the abovementioned meaning and $R^6$ represents a group of the formula $-SO_2R^{12}$ in which $R^{12}$ represents straight-chain or branched alkyl having up to 4 carbon atoms, benzyl or phenyl, each of which is optionally substituted by a straight-chain or branched alkyl having up to 4 carbon atoms, a and b are identical or different and represent a number 0 or 1, $R^7$ represents hydrogen or straight-chain or branched alkyl having up to 6 carbon atoms or acetyl, $R^8$ and $R^{10}$ are identical or different and represent straight-chain or branched alkyl having up to 4 carbon atoms, cyclopropyl, cyclobutyl, cyclopentyl, cyclohexyl or cycloheptyl, phenyl or thienyl, $R^8$ and $R^{11}$ are identical or different and represent hydrogen or straight-chain or branched alkyl having up to 6 carbon atoms, E represents hydrogen, fluorine, chlorine, bromine, trifluoromethyl, carboxyl or straight-chain or branched alkyl, alkoxy or alkoxycarbonyl, each of which has up to 4 carbon atoms, L represents straight-chain or branched alkyl which has up to 6 carbon atoms and which is optionally substituted by cyclopropyl, cyclobutyl, cyclopentyl, cyclohexyl, cycloheptyl or phenyl, or represents cyclopropyl, cyclobutyl, cyclopentyl, cyclohexyl, cycloheptyl or cyclooctyl, each of which is optionally substituted by straight-chain or branched alkyl having up to 4 carbon atoms, $R^1$ represents hydrogen or straight-chain or branched alkyl having up to 6 carbon atoms, $R^2$ represents a radical of the formula $-C(CH_3)_2-CH_2OH$,

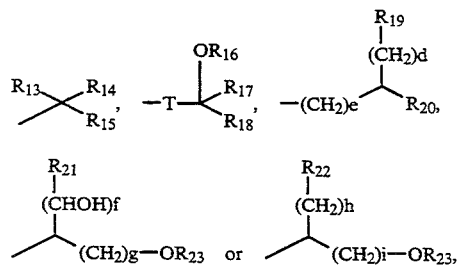

in which $R^{13}$ and $R^{14}$ are identical or different and represent hydrogen or straight-chain or branched alkyl having up to 6 carbon atoms, $R^{15}$ represents straight-chain or branched alkyl which has 2 to 6 carbon atoms and which may also optionally have to be up to disubstituted by identical or different substituents from the series comprising hydroxyl, carboxyl, trifluoromethyl, fluorine, chlorine, bromine, by straight-chain or branched alkoxy, acyl or alkoxycarbonyl, each of which has up to 6 carbon atoms, or by phenyl, naphthyl, furanyl, pyrrolidinyl, thienyl, pyridyl, tetrahydrofuranyl, tetra-hydropyranyl, dihydrobenzopyranyl or dihydrobenzofuranyl, each of which can optionally be substituted by fluorine, chlorine or hydroxyl, or alkyl can optionally be substituted by a group of the formula $-CO-NR_{24}R^{25}$ in which $R^{24}$ and $R^{25}$ have the abovementioned meaning of $R^5$ and $R^6$ and are identical therewith or different therefrom, or $R^{24}$ and $R^{25}$ together with the nitrogen atom form a morpholine ring, or $R_{15}$ represents straight-chain or branched alkoxy or alkoxycarbonyl, each of which has up to 6 carbon atoms, hydroxyl, carboxyl, trifluoromethyl or the group of the formula $-CO-NR^{24}R^{25}$ in which $R^{24}$ and $R^{25}$ have the abovementioned meaning, T represents straight-chain or branched alkyl having from 2 to 6 carbon atoms, $R^{16}$ represents hydrogen or straight-chain or branched alkyl having up to 6 carbon atoms, $R^{17}$ and $R^{18}$ are identical or different and represent hydrogen, straight-chain or branched alkyl having up to 4 carbon atoms or phenyl, or $R^{17}$ and $R^{18}$ together form an indenyl or fluorenyl ring, d represents a number 0, 1, 2 or 3, e represents a number 1, 2 or 3, f represents a number 1, 2 or 3, g represents a number 1, 2, 3, 4 or 5, h represents a number 0, 1, 2 or 3, i represents a number 2, 3 or 4

$R^{20}$ has the abovementioned meaning of $R^{15}$ and is identical therewith or different therefrom or denotes the $-CH_2OH$ group, $R^{19}$, $R^{21}$ and $R^{22}$ are identical or different and represent phenyl which is optionally up to disubstituted by identical or different substituents from the series comprising fluorine, chlorine, bromine, hydroxyl, trifluoromethyl or by straight-chain or branched alkyl or alkoxy, each of which has up to 6 carbon atoms, phenoxy or benzyloxy, $R^{23}$ and $R^{23'}$ are identical or different and represent hydrogen or straight-chain or branched alkyl or alkoxycarbonyl having in each case up to 6 carbon atoms, and their salts.

Particularly preferred compounds of the general formula (I) are those in which

A represents straight-chain or branched alkyl or alkenyl, each of which has up to 4 carbon atoms, or represents cyclopropyl, cyclopentyl or cyclohexyl, G represents hydrogen, fluorine, chlorine or perfluoroalkyl having up to 2 carbon atoms, D represents a group of the formula $-CH_2OR^3$, $-CO-R^4$,

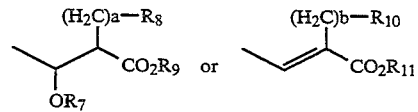

in which $R^3$ represents hydrogen or straight-chain or branched alkyl having up to 4 carbon atoms, $R^4$ represents hydrogen, hydroxyl or straight-chain or branched alkoxy having up to 4 carbon atoms, $R^5$ and $R^6$ are identical or different and represent hydrogen, straight-chain or branched alkyl having up to 4 carbon atoms, or $R^5$ has the abovementioned meaning and $R^6$ represents a group of the formula $-SO_2R^{12}$ in which $R^{12}$ represents methyl, ethyl, benzyl, p-tolyl or phenyl, a and b are identical or different and represent a number 0 or 1, $R^7$ represents hydrogen or straight-chain or branched alkyl having up to 4 carbon atoms, $R^8$ and $R^{10}$ are identical or different and represent cyclopropyl, cyclohexyl or phenyl, $R^9$ and $R^{10}$ are identical or different and represent hydrogen or straight-chain or branched alkyl having up to 4 carbon atoms, E represents hydrogen, fluorine, chlorine, bromine, trifluoromethyl, trifluoromethoxy or methyl, L represents straight-chain or branched alkyl which has up to 4 carbon atoms and which is optionally substituted by cyclopropyl, cyclopentyl, cyclohexyl, cycloheptyl or phenyl, or represents cyclopropyl, cyclopentyl, cyclohexyl, cycloheptyl or cyclooctyl, $R^1$ represents hydrogen or straight-chain or branched alkyl having up to 4 carbon atoms, $R^2$ represents a radical of the formula —C(CH$_3$)$_2$—CH$_2$OH $$\underset{R_{15}}{\overset{R_{13}}{\diagup}}\overset{R_{14}}{\diagdown}, \quad -T-\underset{R_{18}}{\overset{OR_{16}}{\underset{|}{C}}}-R_{17}, \quad -(CH_2)e\underset{R_{20}}{\overset{R_{19}}{\underset{|}{C}(CH_2)d}},$$

$$\underset{(CH_2)g-OR_{23}}{\overset{R_{21}}{\underset{|}{C}(CHOH)f}} \text{ or } \underset{(CH_2)i-OR_{23}}{\overset{R_{22}}{\underset{|}{C}(CH_2)h}},$$

in which $R^{13}$ and $R^{14}$ are identical or different and represent hydrogen or straight-chain or branched alkyl having up to 4 carbon atoms, $R^{15}$ represents straight-chain or branched alkyl which has 2 to 4 carbon atoms and which may have to be substituted by hydroxyl, carboxyl, trifluoromethyl, straight-chain or branched alkoxy, acyl or alkoxycarbonyl, each of which has up to 4 carbon atoms, or by phenyl, pyridyl, furanyl, thienyl, tetrahydrofuranyl or pyrrolidinyl, or represents straight-chain or branched alkoxy or alkoxycarbonyl, each of which has up to 4 carbon atoms, hydroxyl, carboxyl or trifluoromethyl, T represents straight-chain or branched alkyl having from 2 up to 5 carbon atoms, $R^{16}$ represents hydrogen or straight-chain or branched alkyl having up to 4 carbon atoms, $R^{17}$ and $R^{18}$ are identical or different and represent hydrogen, methyl, ethyl or phenyl, or $R^{17}$ and $R^{18}$ together form an indenyl or fluorenyl ring, d represents a number 0, 1 or 2,
e represents a number 1, 2 or 3,
f represents a number 1, 2 or 3,
g represents a number 1, 2, 3 or 4,
h represents a number 0, 1 or 2,
i represents a number 2 or 3, $R^{20}$ has the abovementioned meaning of $R^{15}$ and is identical thereto or different therefrom or denotes the —CH$_2$OH group, $R^{19}$, $R^{21}$ and $R^{22}$ are identical or different and represent phenyl which is optionally substituted by fluorine, hydroxyl, trifluoromethyl or by straight-chain or branched alkyl or alkoxy, each of which has up to 4 carbon atoms, $R^{23}$ and $R^{23'}$ are identical or different and represent hydrogen or straight-chain or branched alkyl or alkoxycarbonyl, each of which has up to 4 carbon atoms, and their salts.

Moreover, a process has been found for the preparation of the compounds of the general formula (I) according to the invention, which is characterised in that compounds of the general formula (II)

$$W-H_2C-\underset{L}{\underset{|}{\overset{E}{\diagup}\diagdown}\text{—CH—CO}_2\text{—Y,}} \quad (II)$$

in which

E and L have the abovementioned meaning

W represents a typical leaving group such as, for example, chlorine, bromine, iodine, tosylate or mesylate, preferably bromine, and Y represents C$_1$–C$_6$-alkyl, are first reacted with imidazoles of the general formula (III)

$$\underset{H}{\overset{N}{\underset{|}{A}}}\diagdown\overset{G}{\underset{N}{\diagup}}\diagdown D, \quad (III)$$

in which

A, B and D have the abovementioned meaning, in inert solvents, if appropriate in the presence of a base and if appropriate under a protective gas atmosphere, to give compounds of the general formula (IV)

$$\underset{A}{\overset{B}{\diagdown}}\underset{N}{\overset{N}{\diagup}}\diagdown\underset{D}{\overset{E}{\diagup}}\text{—CH—CO}_2Y, \quad (IV)$$

in which

A, G, D, E, L and Z have the abovementioned meaning, and, if appropriate after hydrolysis and/or activation has taken place beforehand, subsequently converted into amides using amines of the general formula (V)

HNR$^1$R$^2$ (V), in which $R^1$ and $R^2$ have the abovementioned meaning, in inert solvents if appropriate in the presence of a base and/or of an auxiliary, for example a dehydrating agent, and, if appropriate, the substituents A, B, D and E are introduced by customary methods, for example by reduction, oxidation, alkylation or hydrolysis, or converted into different groups, and, if appropriate, the isomers are separated, and in the case where salts are prepared, reacted with a suitable base or acid.

The process according to the invention can be illustrated by way of example by the following equation:

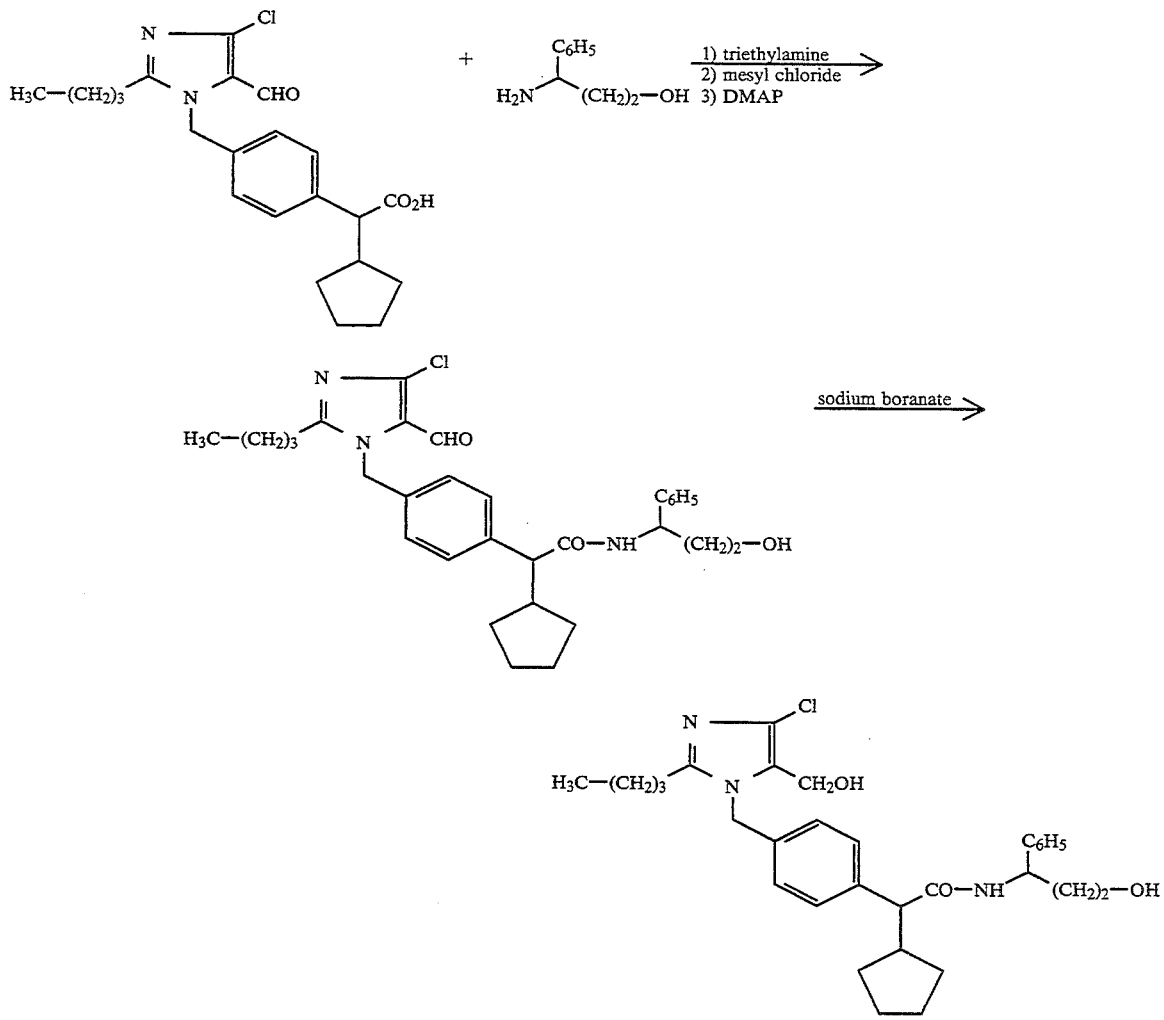

Suitable solvents for the process are customary organic solvents which remain unchanged under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogeno-hydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Dimethylformamide and tetrahydrofuran are preferred.

Bases which can generally be employed in the process according to the invention are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal alcoholates or alkaline earth metal alcoholates such as sodium methanolate, potassium methanolate, sodium ethanolate, potassium ethanolate or potassium tert-butylate, or organic amines (trialkyl($C_1$-$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ, as bases, alkali metals such as sodium or their hydrides, such as sodium hydride. Preferred compounds are sodium hydride, potassium carbonate, triethylamine, pyridine and potassium tert-butylate, DBU or DABCO.

In general, the base is employed in an amount of 0.05 mole to 10 moles, preferably from 1 mole to 2 moles, per mole of the compound of the formula (III).

The process according to the invention is generally carried out in a temperature range from −30° C. to +100° C., preferably from −10° C. to +60° C.

The process according to the invention is generally carried out under atmospheric pressure. However, it is also possible to carry out the process under superatmospheric or subatmospheric pressure (for example in a range from 0.5 to 5 bar). Suitable bases are those inorganic bases customary for hydrolysis. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate, potassium carbonate or sodium hydrogen carbonate, or alkali metal alcoholates such as sodium methanolate, sodium ethanolate, potassium methanolate, potassium ethanolate or potassium tert-butanolate. Lithium hydroxide, sodium hydroxide or potassium hydroxide are particularly preferably employed.

Solvents which are suitable for the hydrolysis are water or those organic solvents which are customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to use mixtures of the abovementioned solvents.

The hydrolysis can also be carried out using acids such as, for example, trifluoroacetic acid, acetic acid, hydrochloric acid, hydrobromic acid, methanesulphonic acid, sulphuric acid or perchloric acid, preferably trifluoro-acetic acid.

The hydrolysis is generally carried out in a temperature range from 0° C. to +100° C., preferably from +20° C. to +80° C.

The hydrolysis is generally carried out under atmospheric pressure. However, it is also possible to carry out the hydrolysis under sub- or superatmospheric pressure (for example from 0.5 to 5 bar).

When carrying out the hydrolysis, the base is generally employed in an amount of 1 to 3 moles, preferably 1 to 1.5 moles, per mole of the ester. It is particularly preferred to use molar amounts of the reactants.

When carrying out the reaction, the first step gives the carboxylates of the compounds according to the invention as intermediates, which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. In this context, it has proved advantageous in the preparation of the carboxylic acids to acidify the basic reaction mixture of the hydrolysis in a second step, without isolating the carboxylates. The acids can then be isolated in the customary manner. In the case of the basic heterocycles, it is also possible to obtain the salts of the heterocycles with the inorganic acids by treating the carboxylate solutions with the abovementioned acids.

Conversion of the compounds of the general formula (IV) into the amides is generally carried out in one of the abovementioned solvents, preferably in tetrahydrofuran or dichloromethane.

If appropriate, the conversion into the amides can be carried out via the activated step of the acid halides [(IV) Y=halogen], which can be prepared from the corresponding acids by reaction with thionyl chloride, phosphorus trichloride, phosphorus pentachloride, phosphorus tribromide or oxalyl chloride.

The conversion into amides is generally effected in a temperature range from −20° C. to +80° C., preferably from −10° C. to +30° C., under atmospheric pressure.

Bases which are suitable for this purpose are, besides the abovementioned bases, preferably triethylamine and/or dimethylaminopyridine, DBU or DABCO.

The base is employed in an amount of 0.5 mole to 10 moles, preferably 1 mole to 5 moles, per mole of the compounds of the general formulae (IV) and (V).

Acid-binding agents which can be employed in the conversion into amides are alkali metal carbonates or alkaline earth metal carbonates such as sodium carbonate, potassium carbonate, alkali metal hydroxides or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[3.4.0]non-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole, or 1,2-oxazolium compounds such as 2-ethyl-5-phenyl-1,2-oxazolium 3-sulphonate, or propanephosphoric anhydride, or isobutyl chloroformate or benzotriazolyloxy-tris-(dimethylamino)phosphonium hexylfluorophosphate or diphenyl phosphonamidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. LEdis, *J. Am. Chem. Soc.* 95, 875 (1973); F. E. Frerman et al., *J. Biol. Chem.* 258, 7087–7093 (1983) and N. B. Benoton, K. Kluroda, *Int. Pept. Prot. Res.*, 17, 197 (1981)].

The acid-binding agents and dehydrating reagents are generally employed in an amount from 0.5 to 3 moles, preferably from 1 to 1.5 moles, per mole of the corresponding carboxylic acids.

The above derivatisation of the substituents A, B, D and E is generally carried out by methods known from the literature, and the reduction of aldehydes or alkoxycarbonyl compounds to, give alcohols (a), the reduction of double bonds (b) and the alkylation (c) will be illustrated by way of example in the following text:

a) The reduction of alkoxycarbonyl compounds or aldehydes to give the corresponding alcohols is generally carried out using hydrides such as lithium aluminium hydride or sodium borohydride, preferably lithium aluminium hydride, in inert solvents such as ethers, hydrocarbons or alcohols or their mixtures, preferably in ethers such as, for example, diethyl ether, tetrahydrofuran or dioxane, or alcohols such as ethanol, in the case of the aldehydes preferably using sodium borohydride in ethanol, in a temperature range from 0° C. to +150° C., preferably from +20° C. to +100° C., under atmospheric pressure.

The reduction of a double bond is generally carried out by hydrogenation using hydrogen in the presence of a catalyst such as, for example, platinum or platinum oxides, rhodium, ruthenium, chlorotris(triphenylphosphine)rhodium, or palladium-on-charcoal, preferably palladium-on-charcoal, in a temperature range from 0° C. to +150° C., preferably from +25° C. to +100° C.

b) Suitable solvents for the hydrogenation are protic solvents such as, for example, methanol, ethanol, and/or aprotic solvents such as, for example, tetrahydrofuran, toluene, dimethylformamide, methylene chloride, dioxane or ethyl acetate. The hydrogenation is carried out at a pressure from 1 to 300 atm, preferably at 1 to 20 atm.

c) The alkylation is generally carried out in one of the above solvents using alkylating agents such as, for example, ($C_1$–$C_8$)-alkyl halides, sulphonates or substituted or unsubstituted ($C_1$–$C_6$)-dialkyl sulphates or ($C_1$–$C_{10}$)-diaryl sulphates, preferably methyl iodide, p-toluenesulphonates or dimethyl sulphate.

Some of the compounds of the general formula (II) are known and can be prepared, for example by first alkylating compounds of the general formula (VI)

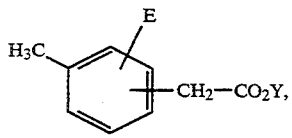

in which

E and Y have the abovementioned meaning, with compounds of the general formula (VII) L-Z (VII), in which L has the abovementioned meaning and Z represents halogen, preferably bromine, in inert solvents, if appropriate in the presence of a base, and, in a second step, carrying out a bromination on the methyl group by the customary method, if appropriate in the presence of a catalyst. The alkylation is generally carried out in one of the above solvents, preferably dimethylformamide, in a temperature range from 0° C. to +70° C., preferably 0° C. to +30° C., and atmospheric pressure.

A suitable starter (catalyst) for the bromination is, for example, azobisisobutyronitrile, dibenzoyl peroxide, preferably azobis isobutyronitrile, the starter being employed in an amount from 0.01 mole to 0.1 mole, preferably from 0.01 mole to 0.05 mole, per mole of the compound of the general formula (VI).

The compounds of the general formula (VI) are known per se or can be prepared by known methods [cf. J. Chem. Soc., Perkin Trans. 1, (9), 1706–1707; J. Chem. Soc., Chem. Commun., (2), 167–168].

The compounds of the general formula (VII) are known per se [cf. Beilstein 5, 19/5, 24/5, 29] or can be prepared from the corresponding alcohols or cycloalkenes by a customary method.

The compounds of the general formula (III) are also known per se [cf., for example, Beilstein 25, 163; 23, 45; U.S. Pat. No. 4,355,040] or can be prepared by a customary method.

The compounds of the general formula (IV), being concrete representatives of the substance, are novel and can be prepared by the above-described process.

The amines of the general formula (V) are known or can be prepared by known processes [cf., for example, Beilstein 11/104, R. V. Vitzgert, Uspekhi, Khimii 32, 3 (1963); Russian Chem. Rev. 32, 1 (1963); Beilstein 4, 87].

The compounds of the general formula (I) according to the invention show a valuable pharmacological spectrum of action which could not have been anticipated.

The compounds according to the invention act as specific A II antagonists since they competitively inhibit the binding of angiotensin II to the receptors. They suppress the vasoconstrictive and aldosteron-secretion-stimulating effects of angiotensin II. Moreover, they inhibit the proliferation of smooth muscle cells.

They can therefore be employed in medicaments for the treatment of arterial hypertension and atherosclerosis. Moreover, they can be employed for the treatment of coronary cardiac diseases, cardiac insufficiency, disturbances of the cerebral performance, ischaemic cerebral diseases, peripheral circulatory disturbances, malfunction of the kidney and adrenal gland, bronchospastic and vascular diseases of the respiratory tract, sodium retention and oedemas.

Test for inhibition of the agonist-induced contraction

Rabbits of both sexes are stunned by a blow on the neck and exsanguinated or, in some cases, anaesthetised with nembutal (approx. 60–80 mg/kg i.v.) and killed by opening the thorax. The thoracic aorta is removed, freed from adhering connective tissue, separated into 1.5 mm wide ring segments and transferred individually, at an initial load of approx. 3.5 g, to 10 ml organ baths held at a temperature of 37° C. and containing a Krebs-Henseleit nutrient solution of the following composition: 119 mmol/l NaCl; 2.5 mmol/l $CaCl_2 \times 2$ $H_2O$; 1.2 mmol/l $KH_2PO_4$; 10 mmol/l glucose; 4.8 mmol/l KCl; 1.4 mmol/l $MgSO_4 \times 7$ $H_2O$ and 25 mmol/l $NaHCO_3$, with carbogen passing through.

The contractions are recorded isometrically by means of Statham UC2 cells via bridge amplifiers (ifd Mülheim or DSM Aalen) and digitised by means of an A/D converter (System 570, Keithley Munich) and evaluated. Agonist dose efficiency curves (DEC) are established early. With each DEC, 3 or 4 individual concentrations are applied to the baths at 4 minute intervals. The end of the DEC and the subsequent washing cycles (16 times in each case approx. 5 sec/min with the above nutrient solution) are followed by a 28 minutes' resting or incubation phase, where the contractions generally resume the initial value.

The height of the, in the normal case 3rd, DEC is used as a reference for assessing the test substance to be tested in further working cycles, increasing dosage rates of the test substance being applied to the baths at the beginning of the incubation time in the subsequent DECs. Each aorta ring is stimulated all day, always with the same agonist.

Agonists and their standard concentrations

| Agonists and their standard concentrations Application volume per individual dose = 100 µl): | | |
|---|---|---|
| KCl | 22.7;32.7;42.7;52.7 | mmol/l |
| 1-Noradrenalin | $3 \times 10^{-9}; 3 \times 10^{-8}, 3 \times 10^{-7}; 3 \times 10^{-6}$ | g/ml |
| Serotonin | $10^{-8}; 10^{-7}; 10^{-6}; 10^{-5}$ | g/ml |
| B-HT 920 | $10^{-7}; 10^{-6}; 10^{-5}$ | g/ml |
| Methoxamin | $10^{-7}; 10^{-6}; 10^{-5}$ | g/ml |
| Angiotensin II | $3 \times 10^{-9}; 10^{-8}; 3 \times 10^{-8}, 10^{-7}$ | g/ml |

The effect at the 3rd = submaximal agonist concentration is used as the basis for calculating the $IC_{50}$ (concentration at which the test substance causes a 50% inhibition).

The compounds according to the invention inhibit the angiotensin II-induced contraction of isolated rabbits' aorta as a function of the dosage rate. Contraction induced by potassium depolarisation or other agonists was not inhibited, or only slightly when high concentrations were used.

TABLE A:

| In vitro inhibition of vasoconstriction in isolated aorta rings of rabbits $IC_{50}$(nM) against contractions, induced by: AII | |
|---|---|
| Example No.: | $IC_{50}$[nM] |
| 11 | 930 |

Blood-pressure measurements on angiotensin-II-infused rats

Male Wistar rats (Moellegaard, Copenhagen, Denmark) having a body weight of 300–350 g are anaesthetised with thiopental (100 mg/kg i.p.). Following tracheotomy, a catheter is inserted into the femoral artery to measure the blood pressure, and a catheter for angiotensin II infusion and a catheter for administrating the substance are inserted into the femoral vein. After administration of the ganglioplegic pentolinium (5 mg/kg i.v.), the infusion of angiotensin II (0.3 μg/kg/min) commences. Once the blood-pressure values have reached a stable level, the test substances are administered either intravenously or orally as a suspension, or solution, in 0.5% Tylose. The changes in blood pressure as an effect of the substance are shown in the table as mean values ±SEM.

Determination of the antihypertensive activity in conscious hypertensive rats

The compounds according to the invention were tested for oral antihypertensive activity on conscious rats by means of surgically-induced unilateral renal artery stenosis. To this end, the right renal artery was constricted by a silver clip of a clear width of 0.18 mm. In this form of hypertension, the plasma renin activity is increased in the first six weeks after the operation. The arterial blood pressure of these animals was subjected to bloodless measurement in defined intervals after administration of the substance using a "tail cuff". Various dosage rates of the test substances were applied intragastrally ("orally") in the form of a suspension in Tylose by garage. The compounds according to the invention lower the arterial blood pressure of the hypertensive rats at a clinically relevant dosage rate.

The compounds according to the invention furthermore inhibit the specific binding of radioactive angiotensin II as a function of the concentration.

Interaction of the compounds according to the invention with the angiotensin II receptor on membrane fractions of the bovine adrenal cortex Bovine adrenal cortices (ACs) which had been removed recently and freed carefully from medulla and capsula are comminuted with the aid of an Ultra-Turrax (Janke & Kunkel, Staufen i.B.) in sucrose solution (0.32M) to give a coarse membrane homogenate which is partially purified in two centrifugation steps to give membrane fractions. Assays with regard to binding with the receptor are carried out on partially purified membrane fractions of bovine AC using radioactive angiotensin II in an assay volume of 0.25 ml which contains, specifically, the partially purified membranes (50–80 μg), $^3$H angiotensin II (3–5 nM), assay buffer solution (50 mM Tris, pH 7.2, 5 mM $MgCl_2$) as well as the test substances. After an incubation time of 60 minutes at room temperature, the sample radioactivity which has not bound is separated by means of moistened glass-fibre filters (Whatman GF/C), and the bound radioactivity is measured in a scintillation cocktail by means of spectrophotometry after the protein has been washed with ice-cold buffer solution (50 mM Tris/HCl, pH 7.4, 5% PEG 6000). The crude data were analysed by computer programs as $K_i$- or $IC_{50}$ values ($K_i$: $IC_{50}$ values corrected for the radioactivity used; $IC_{50}$ values: concentration at which the test substance brings about a 50% inhibition of the specific binding of the radio ligand).

Example 6: $K_i$ = 600 nM
Example 17: $K_i$ = 480 nM

Assay of the inhibition of smooth muscle cell proliferation by the compounds according to the invention To determine the antiproliferative action of the compounds, smooth muscle cells are used which have been obtained from rats' aortas by means of media explant technique [R. Ross, *J. Cell. Biol.* 50. 172, 1971]. The cells are sown in suitable culture dishes, generally 96-well plates, and grown for 2–3 days in medium 199 containing 7.5% of FCS and 7.5% NCS, 2 mM of L-glutamine and 15 mM of HEPES, pH 7.4, in 5% $CO_2$ at 37° C. The cells are then synchronised for 2–3 days by serum starvation, and growth subsequently encouraged by serum or other factors. Test compounds are added simultaneously. After 16–20 hours, 1 μCi of $^3$H thymidine is added, and the incorporation of this substance into the TCA-precipitable cell DNA is determined after a further 4 hours.

To determine the halfmaximal inhibition of thymidine incorporation ($IC_5O$) caused by addition of 10% FCS, the compounds were sequentially diluted in the range of $10^6$M to $10^{-9}$M.

| Ex. 6 | $IC_{50}$= 100 nM |
|---|---|
| Ex. 9 | $IC_{50}$= 38 nM |
| Ex. 13 | $IC_{50}$= 28 nM |

The new active compounds can be converted in the known manner into the customary formulations such as tablets, coated tablets, pills, granules, aerosols, syrups, emulsions, suspensions and solutions, using inert, non-toxic, pharmaceutically acceptable excipients or solvents. The therapeutically active compound should in each case be present in a concentration from approximately 0.5 to 90% by weight of the entire mixture, i.e. in amounts which suffice to reach the dosage range indicated.

The formulations are prepared, for example, by extending the active compounds with solvents and/or excipients, if appropriate using emulsifying agents and/or dispersents, it being possible, if appropriate, for organic solvents to be used as auxiliary solvents, for example when water is used as diluent.

Administration is effected in the customary manner, preferably orally or parenterally, in particular perlingually or intravenously.

In the case of parenteral administration, solutions of the active compound can be employed using suitable liquid excipients.

In general, it has proven advantageous to administer from approximately 0.001 to 1 mg/kg, preferably approximately 0.01 to 0.5 mg/kg, of body weight in the case of intravenous administration so as to achieve effective results, and dosage rates in the case of oral administration are approximately 0.01 to 20 mg/kg, preferably 0.1 to 10 mg/kg, of body weight.

If appropriate, it may be necessary, however, to deviate from the abovementioned amounts, namely as a function of the body weight or the type of administration, the individual behaviour towards the medicament, the nature of its formulation and the time or interval within which administration takes place. Thus, in some cases, it may be sufficient to manage with less than the abovementioned minimum amount, while in other cases the abovementioned upper limit must be exceeded. When greater amounts are administered, it may be recommended to distribute the latter throughout the day in the form of several individual doses.

STARTING COMPOUNDS

Example I

Tert-butyl 4-methylphenyl acetate

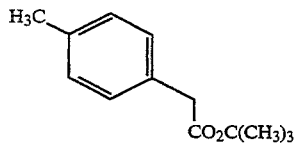

450 g(3 mol) of 4-methylphenyl acetic acid, 1.13 l (12 mol) of tert-butanol and 90 g (0.74 mol) of dimethylaminopyridine are dissolved in 2 l of dichloromethane. After an addition of 680 g (3.3 mol) of dicyclohexylcarbodiimide, dissolved in 400 ml of dichloromethane, the mixture is stirred for 20 hours at 25° C., the urea which has precipitated is filtered off with suction and washed with 200 ml of dichloromethane, and the organic phase is washed in each case twice using 500 ml of 2N hydrochloric acid and water. The organic phase is concentrated and distilled.

Yield: 408 g (66% of theory)
Boiling point: 73°–78° C./0.2 mm

Example II

Tert-butyl 2-cyclopentyl-2-(4-methylphenyl)acetate

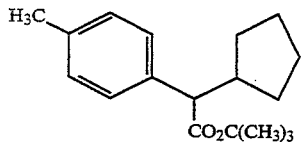

33.5 g (0.3 mol) of potassium tert-butylate are introduced into 100 ml of DMF at 0° C. with the exclusion of moisture, and 51.6 g (0.25 mol) of tert-butyl 4-methylphenyl acetate in 250 ml of DMF are added dropwise. The mixture is stirred for 30 minutes at 0° C., and 32.2 ml (0.3 mol) of cyclopentyl bromide in 150 ml of DMF are added dropwise at 5°–15° C., and the mixture is stirred for 20 hours at 25° C. After concentration, the residue is partitioned between water/diethyl ether, and the ether phase is dried over sodium sulphate and concentrated. The product crystallises. Yield: 67 g (97.5% of theory)

Melting point: 51°–53° C.

Example III

Tert-butyl 2-(4-bromomethyl-phenyl)-2-cyclopentyl-acetate

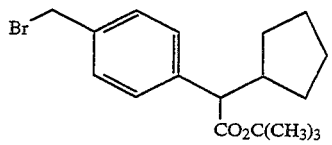

27.4 g (0.1 mol) of tert-butyl 2-cyclopentyl-2-(4-methylphenyl)-acetate are dissolved in 200 ml of carbon tetrachloride and the solution is heated to boiling point. After an addition of 0.82 g of azobisisobutyronitrile, 18.7 g (0.105 mol) of n-bromosuccinimide are added in portions, the mixture is subsequently refluxed for 1 hour and cooled to 0° C., and succinimide is filtered off. After concentration of the filtrate, the product precipitates. It is washed with petroleum ether (40/60) and dried.
Yield: 20 g (57% of theory)
Melting point: 73°–76° C.

Example IV

Tert-butyl 2-[4-(2-butyl-4-chloro-5-formyl-imidazol-1-yl-methyl)-phenyl]-2-cyclopentyl-acetate

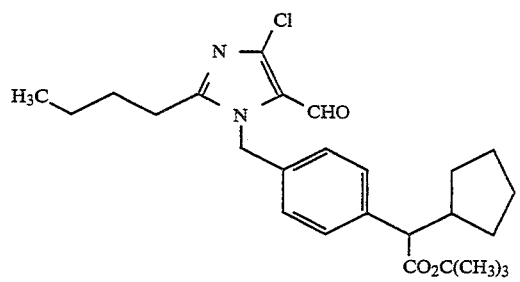

1.6 g (0.053 mol) of sodium hydride (80%) are suspended under protective gas in 50 ml of DMF, 10 g (0.053 mol) of 2-butyl-5-formyl-4-chloroimidazole (preparation as described in EP 324,377) in 100 ml of DMF are added dropwise at 0° C., the mixture is subsequently stirred for 15 minutes at 0° C., and 18.9 g (0.053 mol) of tert-butyl 2-(4-bromomethylphenyl)-2-cyclopentyl-acetate in 100 ml of DMF are added dropwise. Stirring is continued for 2 hours at 0° C., the solvent is evaporated, the residue is taken up in diethyl ether, the mixture is filtered, and the product is concentrated and then chromatographed over silica gel 60 using dichloromethane. Yield: 16.2 g (66.7% of theory)

Melting point: 101°–102° C.

Example V

2-[4-(2-butyl-4-chloro-5-formyl-imidazol-1-yl-methyl)-phenyl]-2-cyclopentyl-acetic acid

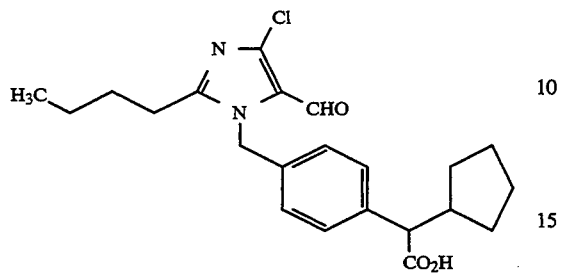

2.3 g (5 mmol) of the compound of Example IV are stirred in 5 ml of dichloromethane and 5 ml of trifluoroacetic acid for 5 hours at 25° C. After concentration, the crude product is chromatographed over silica gel 60 using dichloromethane/methanol (100:5). Yield: 1.8 g (87.6% of theory)

Melting point: 95°–98° C.

PREPARATION EXAMPLES

Example 1

N-(3-Hydroxy-1-phenylpropyl)-2-[4-(2-butyl-4-chloro-5-formyl-imidazol-1-yl-methyl)-phenyl]-2-cyclopentyl acetamide

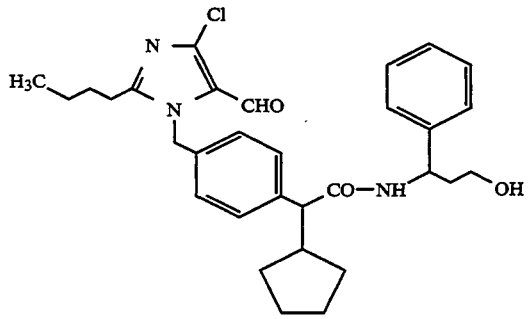

600 mg (1.49 mmol) of the compound of Example V are dissolved in 5 ml of THF, 0.41 ml (2.98 mmol) of triethylamine and 0.13 ml (1.64 mmol) of mesyl chloride are added at −30° C., and the mixture is stirred for 30 minutes. After an addition of 0.18 mg (1.49 mmol) of DMAP, and 0.27 mg (1.79 mmol) of 3-amino-3-phenyl-propan-1-ol in 5 ml of THF, the mixture is stirred for 20 hours at 25° C. After an addition of 20 ml of water, the mixture is acidified using 0.2 ml of glacial acetic acid and extracted three times using 20 ml of ethyl acetate, the organic phase is dried over sodium sulphate and concentrated, and the residue is chromatographed over silica gel 60 using ethyl acetate/petroleum ether [(1:2) via (1:1) to pure ethyl acetate].

Yield: 385 mg (48% of theory) $R_f$=0.66 (dichloromethane: methanol=10:1)

Example 2

N-(3-Hydroxy-1-phenyl-propyl)-2-[4-(2-butyl-4-chloro-5-hydroxymethyl-imidazol-1-yl-methyl)phenyl]-2-cyclopentyl acetamide

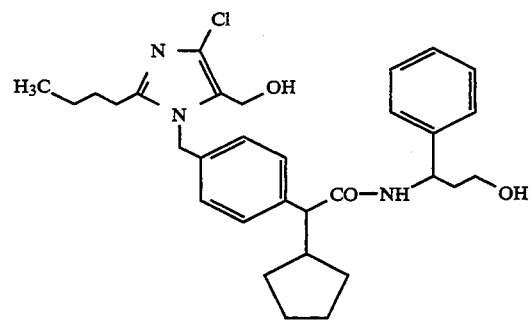

330 mg (0.61 mmol) of the compound of Example 1 are dissolved in 20 ml of methanol and reacted with 24 mg (0.61 mmol) of sodium boranate. After 100 minutes, 20 ml of water are added, and the mixture is acidified using dilute hydrochloric acid and extracted twice using 20 ml of ethyl acetate. The organic phase is dried over sodium sulphate and concentrated.

Yield: 310 mg (94% of theory) $R_f$=0.37 (dichloromethane: methanol=10:1)

Analogously to the protocols of Examples 1 and 2, the examples given in Tables 1, 2, 3 and 4 are prepared in each case depending on the meaning of D:

TABLE 1

| Example No. | D | $R^2$ | $R_f$/ *Solvent | Isomer |
|---|---|---|---|---|
| 3 | —CHO | —(CH$_2$)$_3$—OH | 0.50$^G$ | rac |
| 4 | —CH$_2$OH | —(CH$_2$)$_3$—OH | 0.15$^G$ | rac |
| 5 | —CHO | HO,,,,⸜C$_6$H$_5$ ⸝,,,,OH | 0.52$^a$ | 2 dia/ent |
| 6 | —CH$_2$OH | HO,,,,⸜C$_6$H$_5$ ⸝,,,,OH | 0.36/0.33$^A$ | 2 dia/ent |

TABLE 2
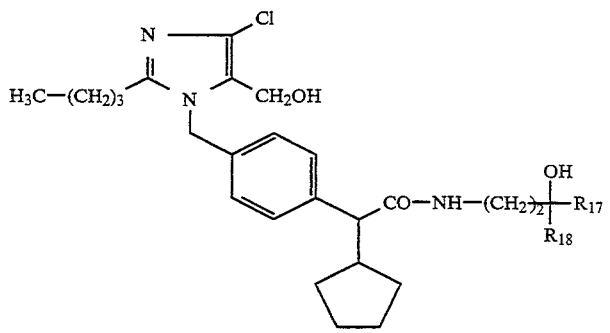
| Example No. | R[17] | R[18] | R$_f$/*Solvent | Yield (% of theory) | Isomer |
|---|---|---|---|---|---|
| 7 | H | —C$_6$H$_5$ | 0.42[C] | 85.1 | 4 dia |
| 8 | —C$_6$H$_5$ | —C$_6$H$_5$ | 0.46[C] | 64.7 | rac |
| 9 | 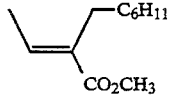 | | 0.44[C] | 83.3 | rac |
TABLE 3
| Example No. | D | R[1] | R[2] | R$_f$/*Solvent | Isomer |
|---|---|---|---|---|---|
| 10 | 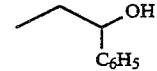 | H |  | 0.74[E] | 4 dia |
| 11 | 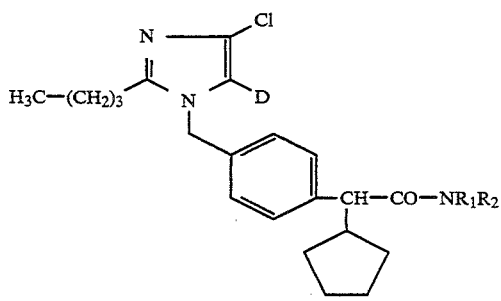 | H |  | 0.38[F] | 4 dia |

TABLE 4

[Structure: imidazole with Cl, D substituent, N-butyl chain, N-CH2-phenyl-CH(cyclopentyl)-CO-N(R1)(R2)]

| Example No. | D | R¹ | R² | R$_f$/*Solvent | Isomer |
|---|---|---|---|---|---|
| 12 | CHO | H | CH(Et)(CH2OH)-phenyl | 0.24 G | 4 dia |
| 13 | CH$_2$OH | H | CH(Et)(CH2OH)-phenyl | 0.53 G | 4 dia |
| 14 | CHO | H | CH(CH3)CH2OH | 0.12 H | 2 dia/ent |
| 15 | CHO | H | CH(CH3)CH(CH3)CH2OH | 0.59 G | 2 dia/ent |
| 16 | CH$_2$OH | H | CH(CH3)CH2OH | 0.33 G | 2 dia/ent |
| 17 | CH$_2$OH | H | CH(CH3)CH(CH3)CH2OH | 0.52 G | 2 dia/ent |
| 18 | CHO | H | C(CH3)2CH2OH | 0.33 G | rac |
| 19 | CH$_2$OH | H | C(CH3)2CH2OH | 0.37 G | rac |

Solvent mixtures
A=Dichloromethane: methanol=50:1
B=Petroleum ether: ethyl acetate=7:3
C=Toluene: acetone=1:1
D=Dichloromethane: Methanol=9:1
E=Petroleum ether: ethyl acetate=3:7
F=Dichloromethane: methanol: glacial acetic acid=9:1:0.1
G=Dichloromethane: methanol=10:1
H=Ethyl acetate: petroleum ether=1:1

Definition of the isomer types:
4dia=Mixture of the 4 diastereomers which are possible when the molecule contains two asymmetric centres
diaA/rac=racemic diastereomer having the higher R$_f$ value
diaB/rac=racemic diastereomer having the lower R$_f$ value
diaA/ent=diastereomer having the higher R$_f$ value (an enantiomer)
diaB/ent=diastereomer having the lower R$_f$ value (an enantiomer)

2dia/ent=mixture of two enantiomerically pure diastereomers
rac=racemate
ent=enantiomer

We claim:
1. A compound of the formula

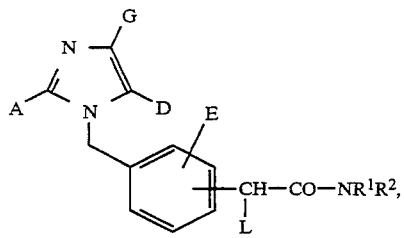

in which
A represents straight-chain or branched alkyl or alkenyl, each of which has up to 8 carbon atoms, or represents cycloalkyl having 3 to 8 carbon atoms,
G represents hydrogen, halogen or perfluoroalkyl having up to 5 carbon atoms,
D represents a group of the formula $-CH_2OR^3$, $-CO-R^4$, $-CO-NR^5R^6$,

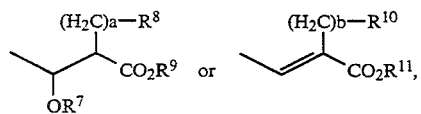

in which
$R^3$ represents hydrogen or straight-chain or branched alkyl having up to 8 carbon atoms,
$R^4$ represents hydrogen, hydroxyl or straight-chain or branched alkoxy having up to 8 carbon atoms,
$R^5$ and $R^6$ are identical or different and represent hydrogen, straight-chain or branched alkyl having up to 8 carbon atoms, or
$R^5$ has the abovementioned meaning and $R^6$ represents a group of the formula $-SO_2R^{12}$ in which
$R^{12}$ represents straight-chain or branched alkyl having up to 6 carbon atoms, benzyl or phenyl, each of which is optionally substituted by straight-chain or branched alkyl having up to 6 carbon atoms,
a and b are identical or different and represent a number 0, 1 or 2,
$R^7$ represents hydrogen or straight-chain or branched alkyl having up to 8 carbon atoms, or a hydroxyl-protective group selected from the group consisting of trimethylsilyl, triethylsilyl, triisopropylsilyl, tert-butyldimethylsilyl, tert-butyldiphenylsilyl, trimethylsilylethoxycarbonyl, benzyl, triphenylmethyl(trityl), monomethoxytrityl (MMTr), dimethoxytrityl (DMtr), benzyloxycarbonyl, 2-nitrobenzyl, 4-nitrobenzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloro-acetyl, 2,2,2-trichloroethyoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)-ethoxy]methyl, 2-(methylthio-methoxy)ethoxycarbonyl, tetrahydropyranyl, benzoyl, 4-methylbenzoyl, 4-nitrobenzoyl, 4-fluorobenzoyl, 4-chlorobenzoyl, and 4-methoxy-benzoyl,
$R^9$ and $R^{10}$ are identical or different and represent hydrogen, straight-chain or branched alkyl having up to 6 carbon atoms, cycloalkyl having 3 to 8 carbon atoms, or phenyl,
$R^9$ and $R^{11}$ are identical or different and represent hydrogen or straight-chain or branched alkyl having up to 8 carbon atoms,
E represents hydrogen, halogen, nitro, hydroxyl, trifluoromethyl, trifluoromethoxy, straight-chain or branched alkyl, alkoxy or alkylcarbonyl, each of which has up to 6 carbon atoms, cyano or carboxyl,
L represents straight-chain or branched alkyl which has up to 8 carbon atoms and which is optionally substituted by cycloalkyl having 3 to 8 carbon atoms or phenyl, or represents cycloalkyl which has 3 to 12 carbon atoms and which is optionally substituted by straight-chain or branched alkyl having up to 6 carbon atoms,
$R^1$ represents hydrogen or straight-chain or branched alkyl having up to 8 carbon atoms,
$R^2$ represents a radical of the formula $-C(CH_3)_2-CH_2OH$,

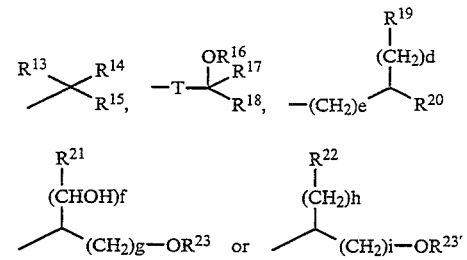

in which
$R^{13}$ and $R^{14}$ are identical or different and represent hydrogen or straight-chain or branched alkyl having up to 8 carbon atoms,
$R^{15}$ represents straight-chain or branched alkyl which has 2 to 8 carbon atoms and which is optionally mono- di- or trisubstituted by identical or different substituents selected from the group consisting of hydroxyl, carboxyl, trifluoromethyl, halogen, nitro, cyano, by straight-chain or branched alkoxy, acyl or alkoxycarbonyl, each of which has up to 8 carbon atoms, or by aryl having 6 to 10 carbon atoms, these substituents, in turn, being optionally mono- or disubstituted by identical or different substituents selected from the group consisting of halogen, nitro, cyano, hydroxyl or by straight-chain or branched alkyl or alkoxy, each of which has up to 6 carbon atoms, or alkyl is optionally substituted by a group of the formula $-CO-NR^{24}R^{25}$ or
$R^{15}$ represents a straight-chain or branched alkylene or alkoxycarbonyl having in each case up to 8 carbon atoms hydroxyl, carboxyl, trifluoromethyl or the group of the formula $-CO-NR^{24}R^{25}$ in which
$R^{24}$ and $R^{25}$ are identical or different and represent hydrogen, straight-chain or branched alkyl having up to 8 carbon atoms, or
$R^{24}$ has the abovementioned meaning and
$R^{25}$ represents a group of the formula $-SO_2R^{12}$
T represents straight-chain or branched alkylene having from 2 up to 8 carbon atoms,
$R^{16}$ is hydrogen or straight-chain or branched alkyl having up to 8 carbon atoms, $R^{17}$ and $R^{18}$ are identical or different and represent hydrogen, straight-chain or branched alkyl having up to 6 carbon atoms or phenyl, or $R^{17}$ and $R^{18}$ together form an indenyl or fluorenyl ring, d represents a number 0, 1, 2, 3 or 4, e represents a number 1, 2, 3 or 4, f represents a number 1, 2, 3 or 4, g represents a number 1, 2, 3, 4, 5 or 6, h represents a number 0, 1, 2, 3 or 4, i represents a number 2, 3, 4 or 5, $R^{20}$ represents straight or branched alkyl which has 2 to 8 carbon atoms and which is optionally mono- di- or trisubstituted by identical or different substituents selected from the group consisting of hydroxyl, carboxyl, trifluoromethyl, halogen, nitro, cyano, by straight-chain or branched alkoxy, acyl or alkoxycarbonyl, each of which has up to 8 carbon atoms, or by aryl having 6 to 10 carbon atoms, these substituents, in turn, being optionally mono- or disubstituted by identical or different substituents selected from the group consisting of halogen, nitro, cyano, hydroxyl or by straight-chain or branched alkyl or alkoxy, each of which has up to 6 carbon atoms, or alkyl is optionally substituted by a group of the formula $-CO-NR^{24}R^{25}$ or denotes a $-CH_2OH$ group, or $R^{15}$ represents a straight-chain or branched alkylene or alkoxycarbonyl having in each case up to 8 carbon atoms hydroxyl, carboxyl, trifluoromethyl or the group of the formula $-CO-NR^{24}R^{25}$ in which $R^{19}$, $R^{21}$ and $R^{22}$ are identical or different and represent phenyl which is optionally mono-, di or trisubstituted by identical or different substituents selected from the group consisting of halogen, hydroxyl, trifluoromethyl, or by straight-chain or branched alkyl or alkoxy, each of which has up to 8 carbon atoms, or by phenoxy or benzyloxy, $R^{23}$ and $R^{23'}$ are identical or different and represent hydrogen, straight-chain or branched alkyl or alkoxycarbonyl, each of which has up to 8 carbon atoms, or its salt.

2. A compound according to claim 1, in which

A represents straight-chain or branched alkyl or alkenyl, each of which has up to 6 carbon atoms, or represents cyclopropyl, cyclobutyl, cyclopentyl, cyclohexyl or cycloheptyl, G represents hydrogen, fluorine, chlorine, bromine or perfluoroalkyl having up to 4 carbon atoms, D represents a group of the formula $-CH_2OR^3$, $-CO-R^4$, $-CO-NR^5R^6$,

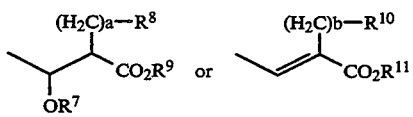

in which $R^3$ represents hydrogen or straight-chain or branched alkyl having up to 6 carbon atoms, $R^4$ represents hydrogen, hydroxyl or straight-chain or branched alkoxy having up to 6 carbon atoms, $R^5$ and $R^6$ are identical or different and represent hydrogen, straight-chain or branched alkyl having up to 6 carbon atoms, or $R^5$ has the abovementioned meaning and $R^6$ represents a group of the formula $-SO_2R^{12}$ in which $R^{12}$ represents straight-chain or branched alkyl having up to 4 carbon atoms, benzyl or phenyl, each of which is optionally substituted by a straight-chain or branched alkyl having up to 4 carbon atoms, a and b are identical or different and represent a number 0 or 1, $R^7$ represents hydrogen or straight-chain or branched alkyl having up to 6 carbon atoms or acetyl, $R^8$ and $R^{10}$ are identical or different and represent straight-chain or branched alkyl having up to 4 carbon atoms, cyclopropyl, cyclobutyl, cyclopentyl, cyclohexyl or cycloheptyl, or phenyl, $R^9$ and $R^{11}$ are identical or different and represent hydrogen or straight-chain or branched alkyl having up to 6 carbon atoms, E represents hydrogen, fluorine, chlorine, bromine, trifluoromethyl, carboxyl or straight-chain or branched alkyl, alkoxy or alkoxycarbonyl, each of which has up to 4 carbon atoms, L represents straight-chain or branched alkyl which has up to 6 carbon atoms and which is optionally substituted by cyclopropyl, cyclobutyl, cyclopentyl, cyclohexyl, cycloheptyl, cyclooctyl or phenyl, or represents cyclopropyl, cyclobutyl, cyclopentyl, cyclohexyl, cycloheptyl or cyclooctyl, each of which is optionally substituted by straight-chain or branched alkyl having up to 4 carbon atoms, $R^1$ represents hydrogen or straight-chain or branched alkyl having up to 6 carbon atoms, $R^2$ represents a radical of the formula $-C(CH_3)_2-CH_2OH$,

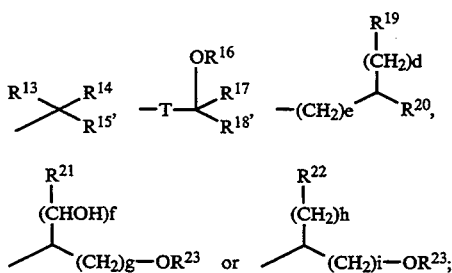

in which $R^{13}$ and $R^{14}$ are identical or different and represent hydrogen or straight-chain or branched alkyl, having up to 6 carbon atoms, $R^{15}$ represents straight-chain or branched alkyl which has 2 to 6 carbon atoms and which is optionally mono- or disubstituted by identical or different substituents selected from the group consisting of hydroxyl, carboxyl, trifluoromethyl, fluorine, chlorine, bromine, by straight-chain or branched alkoxy, acyl or alkoxycarbonyl, each of which has up to 6 carbon atoms, or by phenyl or naphthyl, each of which optionally substituted by fluorine, chlorine or hydroxyl, or alkyl optionally substituted by a group of the formula $-CO-NR^{24}R^{25}$ or $R^{15}$ represents straight-chain or branched alkoxy or alkoxycarbonyl, each of which has up to 6 carbon atoms, hydroxyl, carboxyl, trifluoromethyl or the group of the formula $-CO-NR^{24}R^{25}$ in which $R^{24}$ and $R^{25}$ are identical or different and represent hydrogen, straight-chain or branched alkyl having up to 6 carbon atoms, or R²⁴ has the abovementioned meaning and R²⁵ represents a group of the formula —SO₂R¹²

T represents straight-chain or branched alkylene having from 2 to 6 carbon atoms, R¹⁶ represents hydrogen or straight-chain or branched alkyl having up to 6 carbon-atoms, R¹⁷ and R¹⁸ are identical or different and represent hydrogen, straight-chain or branched alkyl having up to 4 carbon atoms or phenyl, or R¹⁷ and R¹⁸ together form an indenyl or fluorenyl ring, d represents a number 0, 1, 2 or 3, e represents a number 1, 2 or 3, f represents a number 1, 2 or 3, g represents a number 1, 2, 3, 4 or 5, h represents a number 0, 1, 2 or 3, i represents a number 2, 3 or 4, R²⁰ denotes straight-chain or branched alkyl which has to 6 carbon atoms and which is optionally mono- or disubstituted by identical or different substituents selected from the group consisting of hydroxyl, carboxyl, trifluoromethyl, fluorine, chlorine, bromine, by straight-chain or branched alkoxy, acyl or alkoxycarbonyl, each of which has up to 6 carbon atoms, or by phenyl or naphthyl, each of which optionally substituted by fluorine, chlorine or hydroxyl or alkyl optionally substituted by a group of the formula —CO—NR²⁴R²⁵, or denotes straight-chain or branched alkoxy or alkoxycarbonyl, each of which has up to 6 carbon atoms, hydroxyl, carboxyl, trifluoromethyl or the group of the formula —CO—NR²⁴R²⁵, or denotes the —CH₂OH group, R¹⁹, R²¹ and R²² are identical or different and represent phenyl which is optionally mono- or disubstituted by identical or different substituents selected from the group consisting of fluorine, chlorine, bromine, hydroxyl, trifluoromethyl or by straight-chain or branched alkyl or alkoxy, each of which has up to 6 carbon atoms, phenoxy and benzyloxy, R²³ and R²³' are identical or different and represent hydrogen or straight-chain or branched alkyl or alkoxycarbonyl having in each case up to 6 carbon atoms, or its salt.

3. A compound according to claim 1, in which

A represents straight-chain or branched alkyl or alkenyl, each of which has up to 4 carbon atoms, or represents cyclopropyl, cyclopentyl or cyclohexyl, G represents hydrogen, fluorine, chlorine or perfluoroalkyl having up to 2 carbon atoms, D represents a group of the formula —CH₂OR³, —CO—R⁴, —CO—NR⁵R⁶,

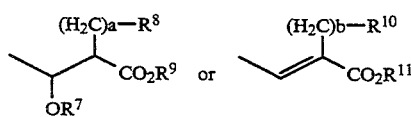

in which

R³ represents hydrogen or straight-chain or branched alkyl having up to 4 carbon atoms, R⁴ represents hydrogen, hydroxyl or straight-chain or branched alkoxy having up to 4 carbon atoms, R⁵ and R⁶ are identical or different and represent hydrogen, straight-chain or branched alkyl having up to 4 carbon atoms, or R⁵ has the abovementioned meaning and R⁶ represents a group of the formula —SO₂R¹² in which R¹² represents methyl, ethyl benzyl p-tolyl or phenyl, a and b are identical or different and represent a number 0 or 1, R⁷ represents hydrogen or straight-chain or branched alkyl having up to 4 carbon atoms, R⁸ and R¹⁰ are identical or different and represent cyclopropyl, cyclohexyl or phenyl, R⁹ and R¹¹ are identical or different and represent hydrogen or straight-chain or branched alkyl having up to 4 carbon atoms, E represents hydrogen, fluorine, chlorine, bromine, trifluoromethyl, trifluoromethoxy or methyl, L represents straight-chain or branched alkyl which has up to 4 carbon atoms and which is optionally substituted by cyclopropyl, cyclopentyl, cyclohexyl, cycloheptyl or phenyl, or represents cyclopropyl, cyclopentyl, cyclohexyl, cycloheptyl or cyclooctyl, R¹ represents hydrogen or straight-chain or branched alkyl having up to 4 carbon atoms, R² represents a radical of the formula —C(CH₃)₂—CH₂OH $$\begin{array}{c}\text{R}^{13}\diagdown\!\!\diagup\text{R}^{14}\\\diagup\!\!\diagdown\text{R}^{15'}\end{array}\!-\text{T}-\begin{array}{c}\text{OR}^{16}\\|\\\text{R}^{17}\\|\\\text{R}^{18'}\end{array}-(\text{CH}_2)_e\diagdown\!\!\diagup\begin{array}{c}\text{R}^{19}\\|\\(\text{CH}_2)_d\\\text{R}^{20},\end{array}$$

$$\begin{array}{c}\text{R}^{21}\\|\\(\text{CHOH})_f\\\diagup\!\!\diagdown(\text{CH}_2)_g\!-\!\text{OR}^{23}\end{array}\quad\text{or}\quad\begin{array}{c}\text{R}^{22}\\|\\(\text{CH}_2)_h\\\diagup\!\!\diagdown(\text{CH}_2)_i\!-\!\text{OR}^{23};\end{array}$$

in which

R¹³ and R¹⁴ are identical or different and represent hydrogen or straight-chain or branched alkyl having up to 4 carbon atoms, R¹⁵ represents straight-chain or branched alkyl which has 2 to 4 carbon atoms and which may be substituted by hydroxyl, carboxyl, trifluoromethyl, straight-chain or branched alkoxy, acyl or alkoxycarbonyl, each of which has up to 4 carbon atoms, or by phenyl, or represents straight-chain or branched alkoxy or alkoxycarbonyl, each of which has up to 4 carbon atoms, hydroxyl, carboxyl or trifluoromethyl, T represents straight-chain or branched alkylene having from 2 up to 5 carbon atoms, R¹⁶ represents hydrogen or straight-chain or branched alkyl having up to 4 carbon atoms, R¹⁷ and R¹⁸ are identical or different and represent hydrogen, methyl, ethyl or phenyl, or R¹⁷ and R¹⁸ together form an indenyl or fluorenyl ring, d represents a number 0, 1 or 2, e represents a number 1, 2 or 3, f represents a number 1, 2 or 3, g represents a number 1, 2, 3 or 4, h represents a number 0, 1 or 2, i represents a number 2 or 3, R20 represents straight-chain or branched alkyl which has 2 to 4 carbon atoms and which may be substituted by hydroxyl, carboxyl, trifluoromethyl, straight-chain or branched alkoxy, acyl or alkoxycarbonyl, each of which has up to 4 carbon atoms, or by phenyl, or represents straight-chain or branched alkoxy or alkoxycarbonyl, each of which has up to 4 carbon atoms, hydroxyl, carboxyl or trifluoromethyl, or denotes the —CH$_2$OH group, $R^{19}$, $R^{21}$ and $R^{22}$ are identical or different and represent phenyl which is optionally substituted by fluorine, hydroxyl, trifluoromethyl or by straight-chain or branched alkyl or alkoxy, each of which has up to 4 carbon atoms, $R^{23}$ and $R^{23'}$ are identical or different and represent hydrogen or straight-chain or branched alkyl or alkoxycarbonyl, each of which has up to 4 carbon atoms.

4. A compound according to claim 1, wherein such compound is N-2-hydroxy-1-hydroxymethyl-2-phenyl-)ethyl-2-[4-(2-butyl-4-chloro-5-formyl-imidazol-1-yl-methyl)phenyl-2-cyclopentylacetamine of the formula

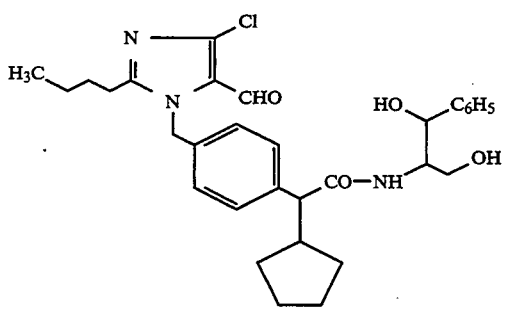

enantiomers or a salt thereof.

5. A compound according to claim 1, wherein such compound is N-(3-hydroxy-3-phenyl)propyl-2-4-(2-butyl-4-chloro-5-hydroxy-methyl-imidazol-1-yl-methyl)phenyl-2-cyclopentylacetamide of the formula

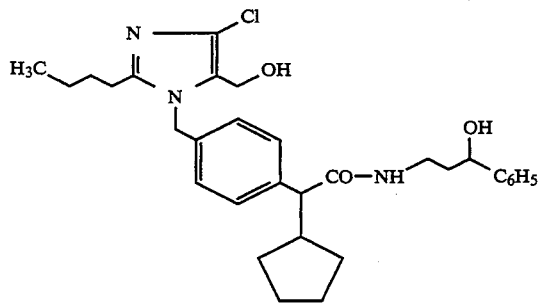

or a salt thereof.

6. A compound according to claim 1, wherein such compound is N-(3-hydroxy-3,3-diphenyl)propyl-2-4-2-butyl-4-chloro-5-hydroxymethyl-imidazol-1-yl-methyl)phenyl-2-cyclobutylacetamide of the formula

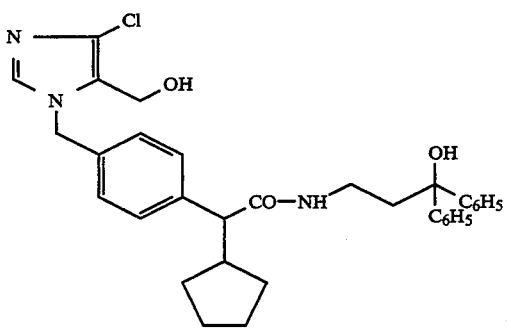

or a salt thereof.

7. A composition for the treatment of atriable hypertension and arteriosclerosis comprising an amount effective therefor of a compound or salt thereof according to claim 1 and a pharmacologically acceptable diluent.

8. The method for treating atriable hypertension and arterisclerosis in a patient in need thereof which comprises administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,420,149
DATED : May 30, 1995
INVENTOR(S) : Muller, et al.

It is certified that error appears in the above-indentified patent and that said Letters Patent is hereby corrected as shown below:

Title Page      [75] Inventors: 6th Inventor after " Walter " delete " Husch " and substitute -- Hubsch --

Col. 25, Line 67,      Delete " $R^9$ " and substitute -- $R^8$ --

Signed and Sealed this

Twenty-third Day of January, 1996

Attest:

BRUCE LEHMAN

*Attesting Officer*      *Commissioner of Patents and Trademarks*